(12) United States Patent
Buchard et al.

(10) Patent No.: US 11,145,414 B2
(45) Date of Patent: Oct. 12, 2021

(54) DIALOGUE FLOW USING SEMANTIC SIMPLEXES

(71) Applicant: Babylon Partners Limited, London (GB)

(72) Inventors: Albert James Thomas Buchard, London (GB); Konstantinos Gourgoulias, London (GB); Max Benjamin Zwiessele, London (GB); Alexandre Khae Wu Navarro, London (GB); Saurabh Johri, London (GB)

(73) Assignee: Babylon Partners Limited, London (GB)

( * ) Notice: Subject to any disclaimer, the term of this patent is extended or adjusted under 35 U.S.C. 154(b) by 0 days.

(21) Appl. No.: 16/289,614

(22) Filed: Feb. 28, 2019

(65) Prior Publication Data

US 2020/0279647 A1    Sep. 3, 2020

(51) Int. Cl.
*G16H 50/20* (2018.01)
*G06N 7/00* (2006.01)
*G06N 5/04* (2006.01)

(52) U.S. Cl.
CPC ............... *G16H 50/20* (2018.01); *G06N 5/04* (2013.01); *G06N 7/005* (2013.01)

(58) Field of Classification Search
CPC ........... G16H 50/20; G06N 5/04; G06N 7/005
See application file for complete search history.

(56) References Cited

U.S. PATENT DOCUMENTS

| 2017/0061324 A1* | 3/2017 | Glass | G06N 7/005 |
| 2018/0046773 A1* | 2/2018 | Tang | G16H 10/60 |
| 2018/0373791 A1* | 12/2018 | Yen | G06F 17/2785 |
| 2019/0371463 A1* | 12/2019 | Asthana | G06K 9/6267 |

OTHER PUBLICATIONS

E. Zdravevski, P. Lameski, A. Kulakov, B. Jakimovski, S. Filiposka and D. Trajanov, "Feature Ranking Based on Information Gain for Large Classification Problems with MapReduce," 2015 IEEE Trustcom/BigDataSE/ISPA, 2015, pp. 186-191, doi: 10.1109/Trustcom.2015.580. (Year: 2015).*

(Continued)

*Primary Examiner* — Evangeline Barr
(74) *Attorney, Agent, or Firm* — McDermott Will & Emery LLP

(57) ABSTRACT

A method for providing a computer implemented medical diagnosis includes receiving an input from a user comprising a symptom of the user. The method also includes providing the symptom as an input to a medical model comprising a probabilistic graphical model comprising probability distributions and relationships between symptoms and diseases, and an inference engine configured to perform Bayesian inference on said probabilistic graphical model. The method also includes generating a question for the user to obtain further information concerning the user to allow a diagnosis, and outputting said question to the user. The method also includes outputting said question to the user, wherein generating a question for the user comprises ranking said questions by determining the utility of the possible questions.

11 Claims, 5 Drawing Sheets

(56) References Cited

OTHER PUBLICATIONS

Araya, M., Buffet, O., and Thomas, V. (2013). Active Diagnosis Through Information-Lookahead Planning. In Journees Francophones de Planication, Decision et Apprentissage pour la conduite de systemes.

Blok, R., Bossen, J. K. J., Hageman, M. G. J. S., Ring, D., and Anderson, J. (2014). Internet Self-Diagnosis in Hand Surgery. Hand, 10(3):565-569.

Friston, K., FitzGerald, T., Rigoli, F., Schwartenbeck, P., ODoherty, J., and Pezzulo, G. (2016). Active inference and learning. Neuroscience & Biobehavioral Reviews, 68:862-879.

Kao, H.-C., Tang, K.-F., and Chang, E. Y. (2018). Context-Aware Symptom Checking for Disease Diagnosis Using Hierarchical Reinforcement Learning. Aaai.

Krause, A. and Guestrin, C. (2005). Optimal nonmyopic value of information in graphical models—Efficient algorithms and theoretical limits. In IJCAI International Joint Conference on Artificial Intelligence.

Krishnamurthy, V. (2002). Algorithms for optimal scheduling and management of Hidden Markov model sensors. IEEE Transactions on Signal Processing, 50(6):1382-1397.

Lucas, P. J., Van Der Gaag, L. C., and Abu-Hanna, A. (2004). Bayesian networks in biomedicine and health-care. Artificial Intelligence in Medicine, 30(3):201-214.

Marzo, J. M., Bernas, G. A., Smolinski, R. J., Bisson, L. J., Rauh, M. A., Komm, J. T., Wind, W. M., and Fineberg, M. S. (2016). How Accurate Are Patients at Diagnosing the Cause of Their Knee Pain With the Help of a Web-based Symptom Checker? Orthopaedic Journal of Sports Medicine, 4(2):232596711663028.

Miller, R. A., Pople, H. E., and Myers, J. D. (1982). Internist-I, an Experimental Computer-Based Diagnostic Consultant for General Internal Medicine. New England Journal of Medicine, 307(8):468-476.

Parsons, J. and Bao, L. (2018). The Value of Information in Retrospect.

Pearl, J. (1988). Probabilistic Reasoning in Intelligent Systems. Elsevier.

Pellegrini, J. and Wainer, J. (2003). On the use of POMDPs to model diagnosis and treatment of diseases. IV Encontro Nacional de Inteligencia Artificial.

Powley, L., McIlroy, G., Simons, G., and Raza, K. (2016). Are online symptoms checkers useful for patients with inflammatory arthritis? BMC Musculoskeletal Disorders, 17(1):362.

Rish, I., Brodie, M., Ma, S., Odintsova, N., Beygelzimer, A., Grabarnik, G., and Hernandez, K. (2005). Adaptive Diagnosis in Distributed Systems. IEEE Transactions on Neural Networks, 16(5):1088-1109.

Semigran, H. L., Levine, D. M., Nundy, S., and Mehrotra, A. (2016). Comparison of Physician and Computer Diagnostic Accuracy. JAMA Internal Medicine, 176(12):1860.

Shortliffe, E. H. (1977). Mycin: A Knowledge-Based Computer Program Applied to Infectious Diseases. In Proceedings of the Annual Symposium on Computer Application in Medical Care.

Zheng, A. X., Rish, I., and Beygelzimer, A. (2005). Efficient Test Selection in Active Diagnosis via Entropy Approximation. Uai—2005, (Jul. 2012).

\* cited by examiner

DIALOGUE FLOW USING SEMANTIC SIMPLEXES

FIELD

Embodiments described herein relate to dialogue flow

BACKGROUND

In a consultation, for example, a medical consultation, a doctor will need to ask questions the patient to determine what is wrong. A human doctor will use a number of skills and techniques for eliciting the correct information from the patient to allow a quick diagnosis of the problem to be made.

To replicate this consultation via a computer, the computer needs to receive a response from the patient and then tailor the next question to efficiently extract information from the patient One possible way of doing this is using Value of Information (VoI) techniques.

DETAILED DESCRIPTION

Figure 1:
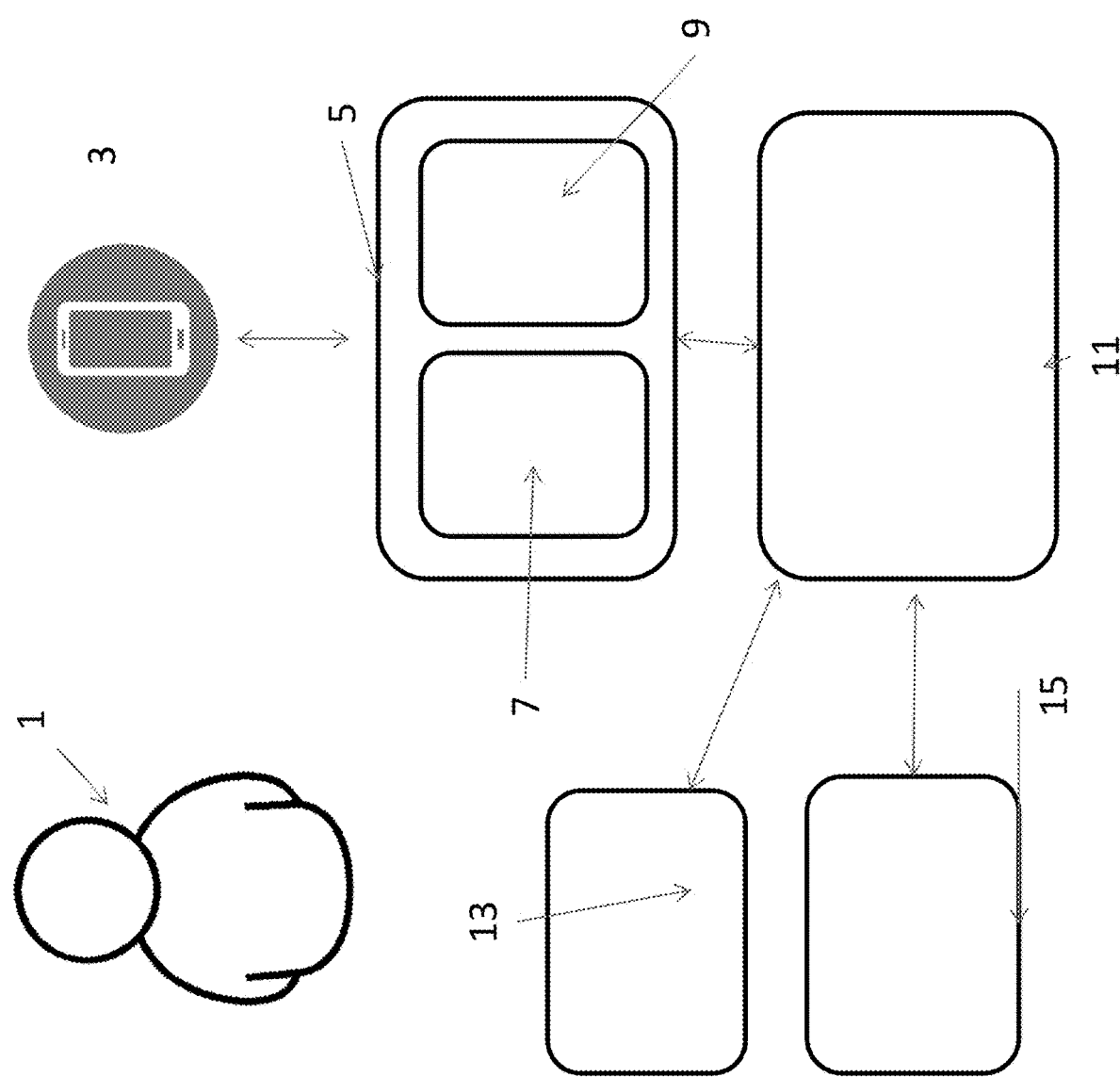
FIG. 1 is a schematic of a system in accordance with an embodiment.

In an embodiment, a method for providing a computer implemented medical diagnosis is provided, the method comprising receiving an input from a user comprising at least one symptom of the user. The method also includes providing the at least one symptom as an input to a medical model comprising a probabilistic graphical model comprising probability distributions and relationships between symptoms and diseases. The medical model also includes an inference engine configured to perform Bayesian inference on said probabilistic graphical model. The method also includes generating a question for the user to obtain further information concerning the user to allow a diagnosis, and outputting said question to the user, wherein generating a question for the user comprises and outputting said question to the user, wherein generating a question for the user comprises ranking said questions by determining the utility of the possible questions, the utility being a measure of the expected information gain determined from the inference engine penalised by the cost incurred by moving the question in semantic space from a previous question.

The disclosed system provides an improvement to computer functionality by allowing computer performance of a function not previously performed by a computer. Specifically, the disclosed system provides for a natural flow of questions from a chatbot. The embodiments described herein address this technical problem by applying a penalty cost to VOI that takes into account changes in the semantic space of the questions. Further, the use of this method allows an embedding of the PGM to be stored offline and hence allows easy fast calculation and retrievable of questions thus increasing speed, realiability and resource utilisation.

A natural flow of questions can be viewed as a Natural/Human-like, consistent flow of questions that improve user experience, sense of trust/consistency.

The Value of Information (VoI) measured as Information Gain is a classic approach to rank the best sequence of tests to conduct during Active Diagnosis. However, in a complex and structured domain such mas medical diagnosis, it might cause the flow of questions to seem unnatural, and affect patient trust in the system.

In an embodiment, the method and system are used with a NoisyOr model crafted for medical diagnosis using case-history alone. In an embodiment, an embedding strategy of evidence nodes over semantic simplices (e.g. anatomical region, or pathogeny) is used and an associated Hamiltonian is used to penalize the VoI of potential questions during online diagnosis. Without significant loss of accuracy or question flow efficiency, the penalized VoI produces more natural flows.

In a further embodiment, the method can be extended to non-myopic setting, to other taxonomies, or produce more complex behaviour by introducing a dynamic energy landscape. In summary, the embodiments described herein propose a computationally efficient method to produce natural case history question flows by introducing a cost related to moving over taxonomic embedding spaces.

A doctor often knows very little about the new patients he receives in consultation. He might know the consultation motive, such as a headache, a rash or a fever, but key information about the patient has yet to be discovered through the process of clinical examination. Active Medical Diagnosis (AMD) is the information gathering process during which a sequence of tests are planned and performed to discover the medical signs that will inform medical diagnosis. As opposed to offline planning, active planning suppose that the sequence of tests is revised as new information is gathered. The types of tests performed in medicine are varied, usually classified in three categories: a) the anamnesis, b) the physical examination, and c) the paraclinical exploration (e.g. lab tests, imagery).

The embodiments described herein focus on the anamnesis, that is the series of questions the physician asks the patient about his medical history or specific symptoms he might present. Planning the best sequence of questions is tightly coupled with the clinician's hypotheses and expectations to produce a quality diagnosis.

Bayesian Networks (BN) or probabilistic graphical models (PGMs) are models for medical diagnosis, indeed they offer a powerful formalism to do inference in highly structured domains and their outputs can be transparently interpreted. However, although amortized inference methods for BNs and PGMs are today a mature technology, active diagnosis remains a challenging problem.

Faced with the task of picking an optimal sequence of questions, heuristics used in probabilistic expert systems often rely on greedy algorithms based on information theoretic value functions such as the Mutual Information or Information Gain (IG).

IG measures the value of information as the marginal reduction of uncertainty over a set of unobserved variables, such as the set of possible causing diseases. Given the assumption that the objective function is submodular, a greedy algorithm will produce question sequences that are close to optimal. However, an IG-based greedy algorithm relies solely on the probabilistic properties of the underlying model and is blind to medical semantic knowledge. As a result, in a very large space of possible questions, such an algorithm may produce sequences of questions which seem unnatural.

In the medical domain, those sequences are characterized by seemingly abrupt changes of context, jumping from one idea to the next without clear intent communicated to the patient, producing poor user experience and affecting the patients trust in the agent. In the embodiments described herein, a method is proposed for embedding medical evidence over semantic simplices and compute a cost associated with changing contexts. Once computed, the cost acts as a penalization of the base Information Gain utility.

In an embodiment, four sets of independent properties are described: gross anatomical region, specific anatomical region, pathogeny (e.g Trauma, Infection), and clinical system (e.g Urology, Neurology). Beyond being understandable, validated, and complete, explicit spaces offer several advantages compared to more complex methods of embedding. Contrary to the other embedding methods explicit spaces offer a guarantee that larger distances will indeed represent a perceivable jump in the flow of question while smaller distance will remain in the same semantic region. This "natural family preservation" is not guaranteed with other embedding methods which might reproduce equally unintelligible clustering. The embodiments described herein produce sequences that are perceived as more consistent to the user, without significant impact on the quality of the diagnosis.

In an embodiment, the semantic space is represented by at least one semantic simplex defining an embedded space. For example, the simplex may be a 3-simplex, but other forms of simplex could be used.

In an embodiment, the vertices of the simplex are elements of the semantic space and wherein the dot product of two elements at distinct vertices is null.

The embedded spaces may be selected from, for example, at least one of Pathogenesis and body systems. Multiple semantic simplexes may be used, each determining a cost and those costs being added to determine the penalty.

In an embodiment, the probabilistic graphical model comprises nodes and said nodes are embedded in said at least one semantic simplex. The probabilistic graphical model may comprise nodes relating to diseases, risk factors and symptoms.

The embedded nodes of said graphical model may be stored in a memory and retrieved for calculating the cost incurred by moving the question in semantic space from a previous question. This task can be done off-line. The nodes may be embedded by a human scoring the nodes against the embedded spaces.

The cost may be determined in a number of different ways which are described later. The energy defined by the simplex may be fixed or dynamic.

FIG. 1 is a schematic of a diagnostic system. In one embodiment, a user 1 communicates with the system via a mobile phone 3. However, any device could be used, which is capable of communicating information over a computer network, for example, a laptop, tablet computer, information point, fixed computer etc.

The mobile phone 3 will communicate with interface 5. Interface 5 has 2 primary functions, the first function 7 is to take the words uttered by the user and turn them into a form that can be understood by the inference engine 11. The second function 9 is to take the output of the inference engine 11 and to send this back to the user's mobile phone 3.

In some embodiments, Natural Language Processing (NLP) is used in the interface 5. NLP helps computers interpret, understand, and then use everyday human language and language patterns. It breaks both speech and text down into shorter components and interprets these more manageable blocks to understand what each individual component means and how it contributes to the overall meaning, linking the occurrence of medical terms to the Knowledge Graph. Through NLP it is possible to transcribe consultations, summarise clinical records and chat with users in a more natural, human way.

However, simply understanding how users express their symptoms and risk factors is not enough to identify and provide reasons about the underlying set of diseases. For this, the inference engine 11 is used. The inference engine is a powerful set of machine learning systems, capable of reasoning on a space of >100s of billions of combinations of symptoms, diseases and risk factors, per second, to suggest possible underlying conditions. The inference engine can provide reasoning efficiently, at scale, to bring healthcare to millions.

In an embodiment, the inference engine comprises a PGM, for example of the type described with reference to FIG. 2.

In an embodiment, the Knowledge Graph 13 is a large structured medical knowledge base. It captures human knowledge on modern medicine encoded for machines. This is used to allows the above components to speak to each other. The Knowledge Graph keeps track of the meaning behind medical terminology across different medical systems and different languages.

In an embodiment, the patient data is stored using a so-called user graph 15.

Figure 2:
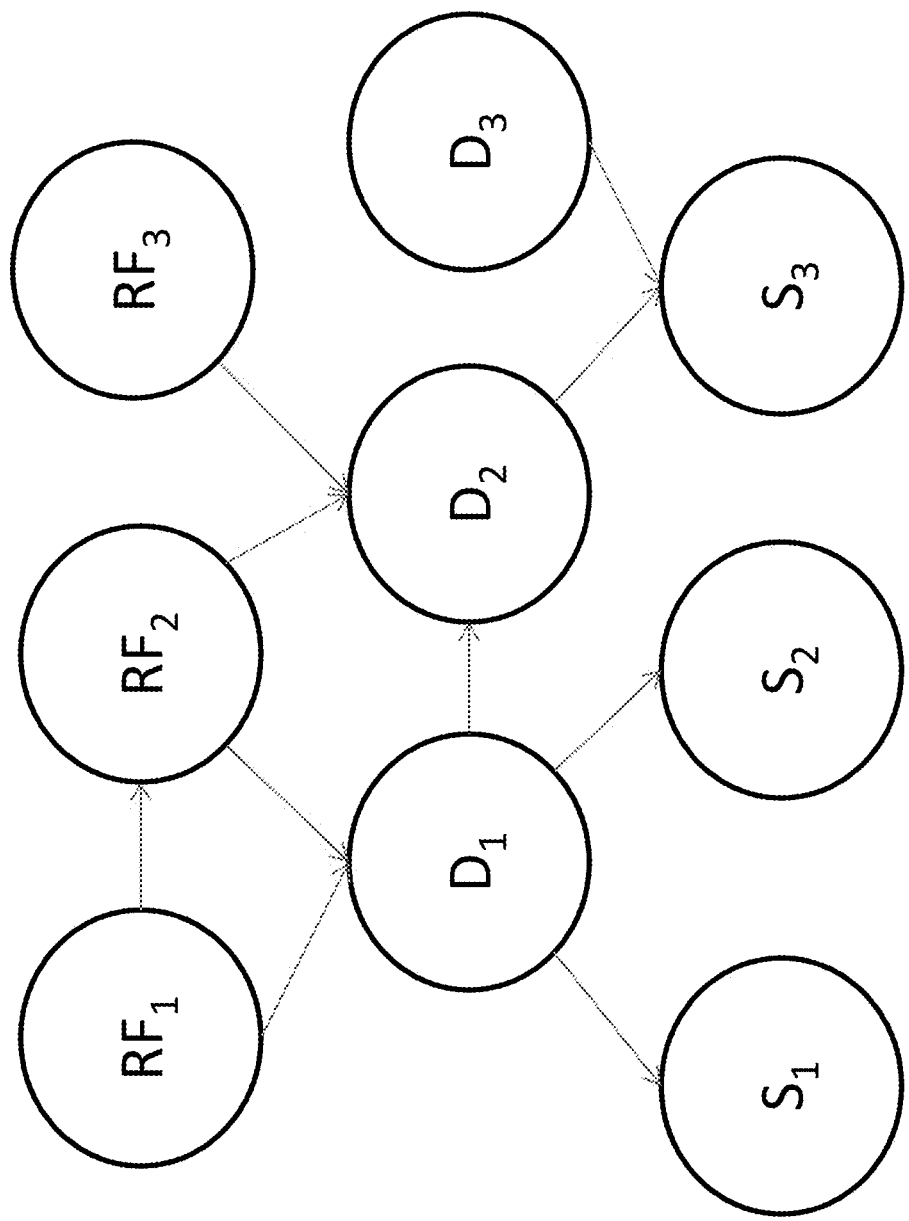
FIG. 2 is a schematic of a probabilistic graphical model.

FIG. 2 is a depiction of a graphical model of the type used in the system of FIG. 1.

The graphical model provides a natural framework for expressing probabilistic relationships between random variables, to facilitate causal modelling and decision making. In the model of FIG. 2, when applied to diagnosis, D stands for diagnosis, S for symptom and RF for Risk Factor. Three layers: risk factors, diseases and symptoms. Risk factors causes (with some probability) influence other risk factors and diseases, diseases causes (again, with some probability) other diseases and symptoms. There are prior probabilities and conditional marginals that describe the "strength" (probability) of connections. In embodiments, noisy-OR and noisy-MAX modelling assumptions are used.

In this simplified specific example, the model is used in the field of diagnosis. In the first layer, there are three nodes $S_1$, $S_2$ and $S_3$, in the second layer there are three nodes $D_1$, $D_2$ and $D_3$ and in the third layer, there are two nodes $RF_1$, $RF_2$ and $RF_3$.

In the graphical model of FIG. 2, each arrow indicates a dependency. For example, $D_1$ depends on $RF_1$ and $RF_2$. $D_2$ depends on $RF_2$, $RF_3$ and $D_1$. Further relationships are possible. In the graphical model shown, each node is only dependent on a node or nodes from a different layer. However, nodes may be dependent on other nodes within the same layer.

In an embodiment, the graphical model of FIG. 2 is a Bayesian Network. In this Bayesian Network, the network represents a set of random variables and their conditional dependencies via a directed acyclic graph. Thus, in the network of FIG. 2, given full (or partial) evidence over symptoms $S_1$, $S_2$ and $S_3$ and risk factors $RF_1$, $RF_2$ and $RF_3$ the network can be used to represent the probabilities of various diseases $D_1$, $D_2$, and $D_3$.

The embodiments described herein relate to the inference engine and processes around the inference engine 11 that provide the interface 5 with information to ask the next question of the patient.

Figure 3:
FIG. 3 is a flow chart showing a method in accordance with an embodiment.

Turning now to FIG. 3, in step S101, the user inputs, for example, "I have a headache". This is passed through the interface 5 of FIG. 1 that will be able to identify from the phrase "I have a headache" which nodes of the PGM should be activate in step S105.

In step S105, the possible next questions are ranked using a structured VOI strategy.

The highest value question is selected in step S107 and then output in step S109. The user input is received in step S111 and this is returned to the diagnostic engine in S103 to allow the next question to be calculated.

When using the structured VOI as described below, the cost may be measured with respect to the previous question or an average of the previous questions.

In an embodiment, the structured VOI strategy computes a cost for the information gain associated with a new piece of evidence ($VOI_{std}$) and penalises this with the cost incurred by moving the question in semantic space from the previous questions ($Cost_{Sem}$).

Thus, an expected utility (EU) is defined:

$$EU = VOI_{std} - Cost_{Sem}$$

The questions are then ranked using the above expected utility.

Next, a description will follow concerning a method for estimating $VOI_{std}$. This will be followed with a description of how Semantic simplexes are used to penalise the cost $Cost_{Sem}$. Finally, there will be an explanation of improvements to estimating $VOI_{std}$ that can be combined with $Cost_{Sem}$ Estimating $VOI_{std}$ The Information Gain associated with a new piece of evidence $E_1$ is defined as the expected reduction of conditional entropy of a set of query variables $D = \{D_0, \ldots, D_k\}$ conditioned on $E_i$. To account for the current state of the diagnostic process, an initial evidence set attribution $E0 = \{E_0 = e_0, \ldots, E_m = e_m\}$, $m \neq i$.

$$IG(D; \varepsilon_0, E_i) = H(D|\varepsilon_0) - H(D|\varepsilon_0, E_i) \quad (1)$$

With $H(D|\varepsilon_0)$, the entropy of the query set D conditioned on the evidence set attribution $\varepsilon_0$. With $\mathcal{D}$ the image of the query set D:

$$H(D | \varepsilon_0) = -\sum_{d \in \mathcal{D}} P(d | \varepsilon_0) \log[P(d | \varepsilon_0)] \quad (2)$$

H(D|E; Ei) is the expected conditional entropy marginalized over the domain of Ei $$H(D | E, E_i) = -\sum_{e_i \in \text{dom } E_i} P(e_i | \varepsilon_0) \sum_{d \in \mathcal{D}} P(d | \varepsilon_0, e_i) \log[P(d | \varepsilon_0, e_i)] \quad (3)$$

In the context of medical diagnosis, the query variables are diseases with attributions $d_i \in \{D_i = \text{"Present"}; D_i = \text{"Absent"}\}$. As the size of the query set increases, computing the joint probability $p(d_1, \ldots, d_k | \varepsilon_0)$ rapidly becomes intractable.

Under assumptions that the query variables $D_1; : : : ; D_k$ are conditionally independent given the evidence set $\varepsilon_0$, and using the chain rules of the joint entropy given by:

$$H(X_1, X_2, \ldots, X_n | Y) = \sum_{i=1}^{n} H(X_i | X_1, \ldots, X_{i-1}, Y) \quad (4)$$

It is possible to rewrite the information gain as a sum of marginal gain for each diseases $D_j$:

$$IG(D; \varepsilon_0, E_i) = \sum_{j=0}^{k} H(D_j | \varepsilon_0) - H(D_j | \varepsilon_0, E_i) \quad (5)$$

Under a similar assumption of conditional independence the Information Gain is sub-modular with respect to the evidence set. The importance of this property lies in the fact that greedy algorithms relying on sub-modular value functions are close to optimal.

The VOI strategy uses a modified version of the Information Gain, weighted by the current posterior marginal of each disease being present, and further normalized between 0 and 1.

This Expected Information Gain $V(E_i; \varepsilon_0)$, biases the heuristic towards confirming the most probable disease first.

$$V(E_i; \varepsilon_0) = \sum_{j=0}^{k} P(D_j = \text{Present} | \varepsilon_0) \frac{IG(D_k; \varepsilon_0, E_i)}{H(D_k | \varepsilon_0)} \quad (6)$$

It is worth noting that the Expected Information Gain is not sub-modular, due to the normalization procedure and the dynamic nature of the top disease set.

In an embodiment, VOI strategy is used with a myopic greedy algorithm which picks the question associated to the evidence node $E_{max}$ with the maximum expected information gain $V(E_{max}; \varepsilon_0)$. The query variable set is restricted to the Top-3 disease set $D = \{(D_1; D_2; D_3\}$, ordered by the diseases marginal posteriors. The algorithm computes the VOI of each element of the set $E^D = \{E_0; : : : ; E_k\}$, composed of the evidence nodes $E_i$ connected to any of the three diseases in D. This requires four inference calls: a) one to order the diseases by their posteriors given the current evidence set $P(d_i|\varepsilon_0)$ as well as to get the posterior marginals of all unobserved evidence nodes $P(e_i|\varepsilon_0)$ and b) three to compute the marginal posteriors of each evidence nodes given each disease in the top set $P(e_i|\varepsilon_0, d_i)$—with assignments $e_i$ and $d_i$ for $E_i$ and $D_i$ respectively. Those three calls allow for the computation of $P(d_i|\varepsilon_0, E_i)$ through Bayes rule:

$$P(d_i | \varepsilon_0, e_i) = \frac{P(e_i | \varepsilon_0, d_i) P(d_i | \varepsilon_0)}{P(e_i | \varepsilon_0)} \quad 6.1$$

The algorithm then picks the evidence node with the maximum VOI, and propose the question related to that node:

$$E_{max} = \underset{E_i}{\mathrm{argmax}} \ VOI(E_i; \varepsilon_0) \quad 6.2$$

Estimating $Cost_{Sem}$

As described, $V(E_i; \varepsilon_0)$ allows to rank evidences $E_i$ relative to how much reduction in uncertainty they might offer over the set of diseases defined in the network. But the measure overlooks completely how natural the flow of subsequent questions might feel to the patient, and often result in question sequence that seem jumpy, and lacking intent.

To mitigate this effect, in an embodiment, a new expected utility EU is defined as Value of Information which penalize V with two costs (one for each embedding spaces) proportional to the change of context produced by asking $E_i$ given the two state vector $s_t^B$ and $s_t^P$ are defined as the average embedding space respectively. $s_t^B$ and $s_t^P$ are defined as the averaged embedding of the set of n previous questions asked. In a further embodiment, the state could be defined in another way, for example taking the average embedding of the current top disease hypothesis. Other methods are also possible, for example: 1) As a function of the embedding of the set of n previous questions asked, 2) As a function of the embedding of the set of current top diseases. The state could also be defined dynamically across time, for example taking 5 diseases at time t=0 and 2 disease at time t=10

$$EU_{\alpha\beta}(E_i;\varepsilon_0,s_t^B,s_t^P) = V(E_i;\varepsilon_0) - \beta C^B(E_i;s_t^B) - \alpha C^P(E_i;s_t^P) \quad (7)$$

These two costs $C^B(E_i; s_t^B)$ and $C^P(E_i; s_t^P)$ are defined over the body systems and pathogenesis spaces respectively. As explained in more detail in the next sections, they are defined as the maximum difference in energy along the path between the current state as defined by the average simplex embedding of the past n answers given by the patient, and the target state defined by the simplex embedding of $E_i$.

In an embodiment, two taxonomies are used over which Diseases, Symptoms and Risk Factors are embedded. Diseases and Risk Factors are more naturally embedded over the space of etiological mechanisms.

Each disease can be categorized by their pathogenesis mechanisms. This is simple yet powerful way to cluster diseases and guide symptom exploration in a natural way (e.g if you are currently asking about infectious diseases you would have to pay a cost to move to trauma). Alternatively this categorization is often used by internal medicine specialist to make sure they exhaust the whole range of differentials when faced with a difficult case. It offers both clear differentiation between categories and the ability to group questions in a natural order while exhausting each categories.

| Pathogenesis types |
| --- |
| Vascular |
| Iatrogenic |
| Infectious |
| Inflammatory |
| Idiopathic |
| Traumatic |
| Tumor |
| Toxic |
| Endocrine/Metabolic |
| Congenital |
| Degenerative |

Although symptoms are often associated with particular systems as taught in medical schools (e.g. cardiovascular, neurological, respiratory) it is often less straightforward to associate symptoms to any particular underlying mechanisms (e.g. shortness of breath). Symptoms are more readily embedded as constitutional symptoms (e.g. fever, asthenia) or as being part of a body system.

| Body systems/Constitutional (i.e general) |
| --- |
| Eyes |
| Ears Nose Mouth Throat (ENT) |
| Cardiovascular |

| Body systems/Constitutional (i.e general) |
| --- |
| Respiratory |
| Gastrointestinal |
| Genitourinary |
| Musculoskeletal |
| Integumentary/Skin/Glands/Breast |
| Neurological |
| Psychiatric |
| Endocrine |
| Haematologic/Lymphatic |
| Allergic/Immune |

The above description relates to two embeddings. The lists of types are given as an example only and other lists could be used. Also, other embeddings could be used and the number of embeddings could be extended, for example four or more semantic spaces described herein are derived from properties of medical concepts used in the PGM: gross anatomical location, pathogenesis, specific anatomical location, and clinical system. A natural embedding for a set of independent characteristic (e.g. location: knee and location: head) is a p-simplex with at each vertex one of the p elements of the semantic space. This space preserves the empty intersection of two distinct characteristics in that the dot product of two points at two distinct vertexes is null.

The expected utility EU of equation (7) can be defined which penalizes the expected utility gain V with four or more costs (one for each embedding spaces) proportional to the change of context produced by asking $E_i$ given the four state vectors $s_t^k$. Each state vector $s_t^k$ is a point in the embedding p-simplex defined as the averaged embedding of the previous questions over each embedding space $$EU(E_i;\varepsilon_0, S_t) = V(E_i;\varepsilon_0) - \sum_k \beta_k C^k(E_i;s_t^k) \quad (10)$$

With $S_t$ the set of all four state vectors $s_t^k$, $\beta_k$ a weight specific for each embedding space, and $C^k$ the cost function for each embedding space.

Figure 4:
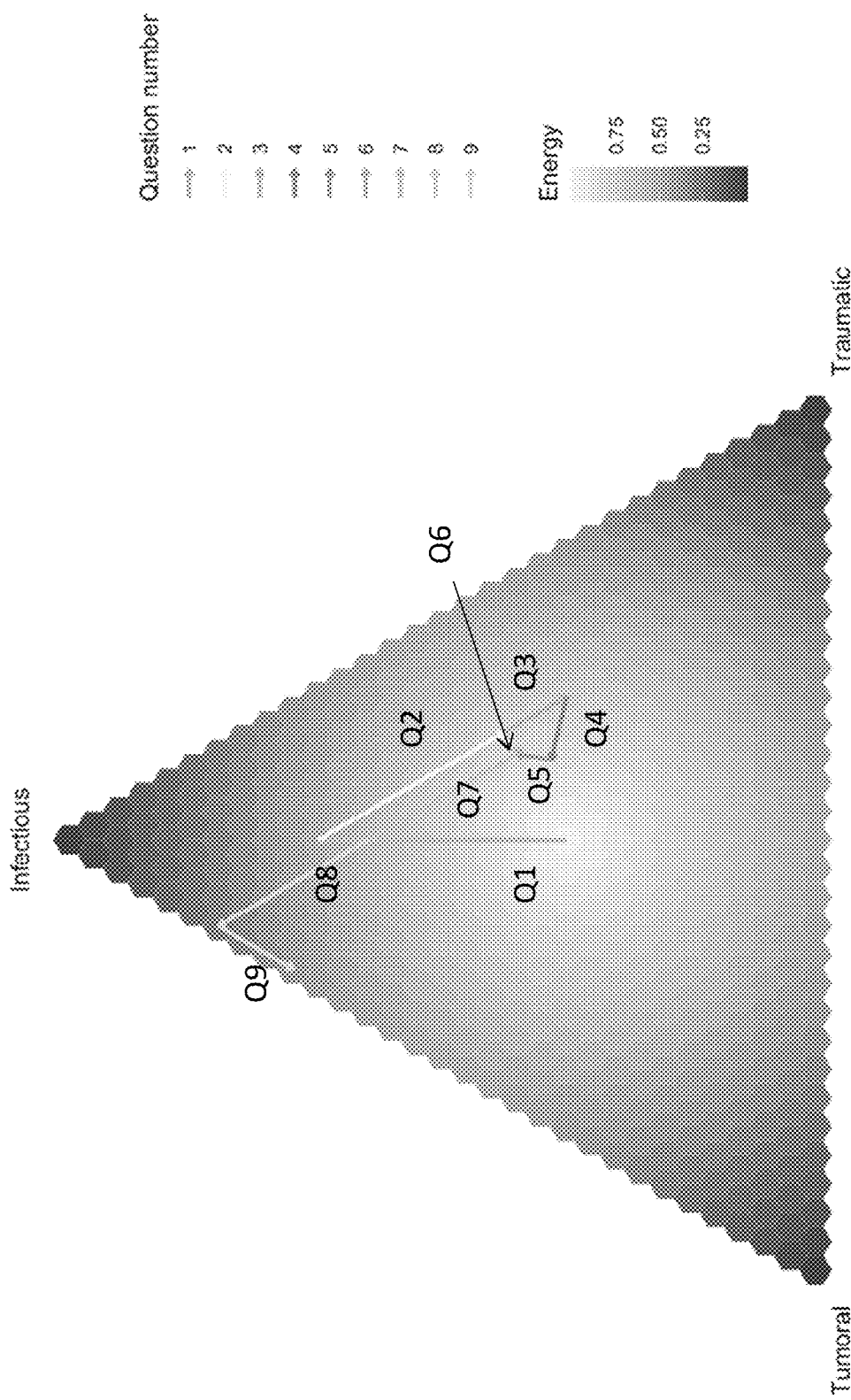
FIG. 4 is a representation of a question flow in a simplex.
Figure 5:
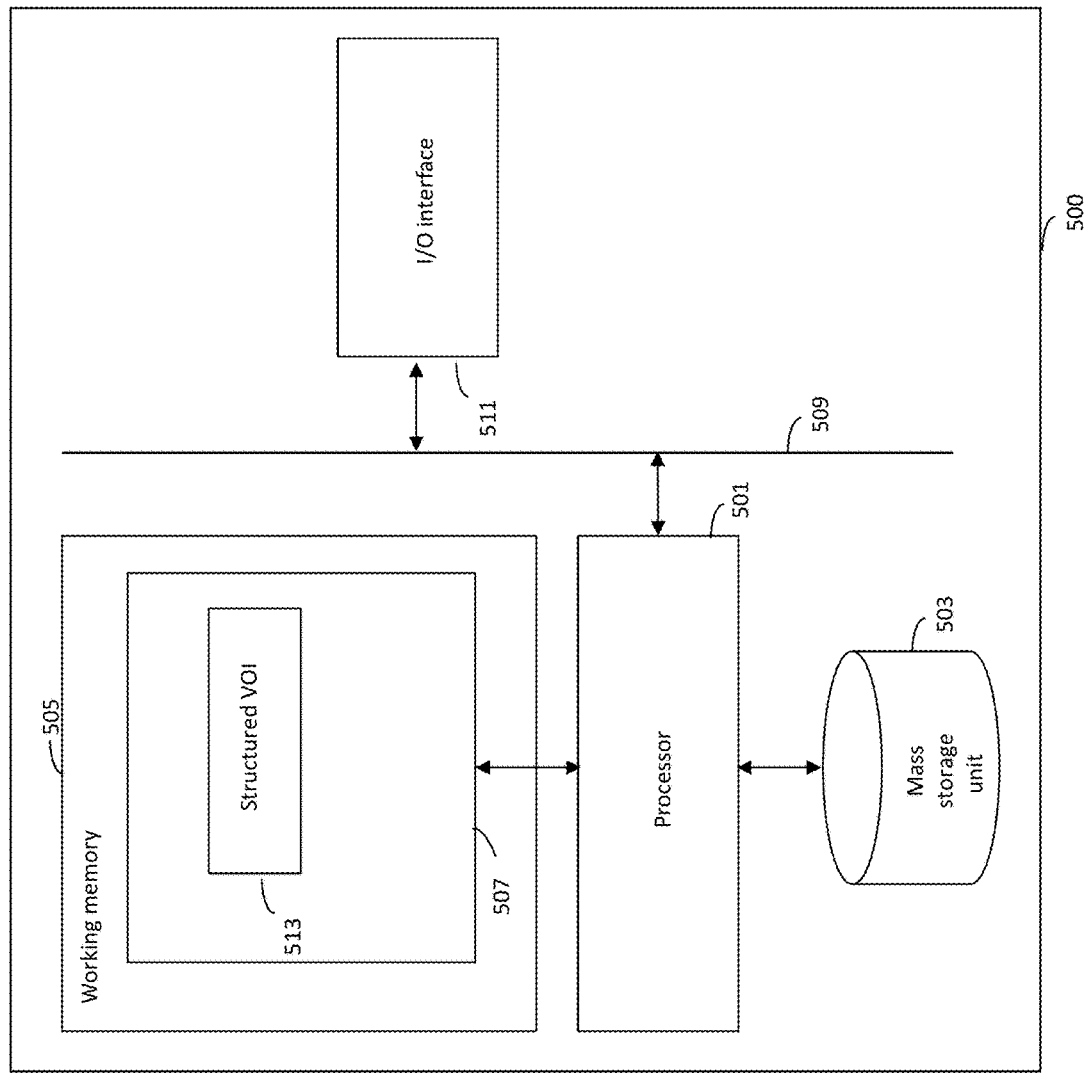
FIG. 5 is a system in accordance with an embodiment.

A sample trajectory over a 3-simplex example is presented in FIG. 4.

The three types of nodes described in the model are Diseases, Symptoms, and Risk Factors. Symptoms and Risk Factors are referred as the evidence nodes $E_i$. As a first embedding step, each type of nodes will be embedded in the taxonomy most relevant to its type.

Experts associate each diseases and risk factors with one or several pathogenesis mechanisms: Flu will be associated to Infection, Tibia fracture with Trauma, Vestibular Schwannoma with Tumoral etc. Each of those m mechanisms sit at one of the vertex of the unit m-simplex, and the embedding of each disease is taken as the average embedding of each of its associated mechanism. Given m pathogenesis types, each disease $D_i$ and risk factor $R_i$ is associated with a vector embedding on the m-simplex $T_{D_i}^P$, $T_{R_i}^P \in [0, 1]^m$. If the disease is not readily classifiable or associated with more than three mechanisms it is classified as "Multiple". In other embodiments, if the disease is not readily classifiable, the embedding of the node is a function of the embedding of its parents and children nodes embedding in the PGM.

A similar process produces embedding of symptoms $S = \{S_0; ::: ; S_p\}$ $T_{S_i}^P \in [0, 1]^l$ on the body system l-simplex. Each disease and risk factor is associated via the PGM with a set of symptoms. By averaging the embedding of their related symptoms, an embedding over body systems for the Risk Factors and Diseases is produced. And respectively, averaging the embedding of related risk factors and diseases produces pathogenesis embedding for the symptoms.

In an embodiment, the current state of the flow is represented as the average embedding of the evidences queried of the n previous steps $\{E_{t-n}; \ldots ; E_{t-1}\}$:

$$s_t = \frac{1}{n-1}\sum_{j=1}^{n} T_{E_{t-j}} \qquad (8)$$

When a new evidence $E_{t-1}$ is given the state changes from $s_{t-1}$ to $s_t$, and it is by exploiting this transformation that costs $C^B(E_{t-1}; s_{t-1}^P)$ and $C^P(E_{t-1}; s_{t-1}^B)$ can be computed.

The embedding of a negative evidence being ambiguous in this context, we only consider positive evidence to approximate the transformation from $s_{t-1}$ to $s_t$.

A transformation function $v_\alpha$ is defined such that:

$$v_\gamma=(s_{t-1},T_{E_{t-1}})=\gamma(T_{E_{t-1}}-s_{t-1}) \qquad (9)$$

With $\gamma$ defined as the velocity, which modulates the how abrupt changes are penalized.

Then $s_t$ is approximated by:

$$\hat{s}_t = s_{t-1} + v_\gamma(s_{t-1}, T_{E_{t-1}}) \qquad (10)$$

In order to improve the consistency of question over the taxonomic spaces in an embodiment, a Hamiltonian is defined of maximum potential at the barycenter of the simplex and zero-potential at the vertices.

L2 Landscape $$H(X) = H_{max} \times \left(1 - \frac{\|X - C\|_2}{\|V_i - C\|_2}\right) \qquad (11)$$

The cost of a transition is computed as the maximum of energy differential on the path between the current state $s_{t-1}$ and $\hat{s}_t$ the approximate next state location.

While a fixed energy landscape improves the naturalness metrics, one could easily introduce more complex behaviour by allowing for the landscape to change during the flow. One possible such heuristic is surprise.

Surprise

Defining a fixed energy landscape can have the detrimental effect of locking the state in regions of lower energy although the question elicited in the region do not produce any positive evidence. To mitigate this effect we can consider time steps eliciting negative evidence as "surprise episodes" producing a temporary collapse of the energy landscape making it easier to escape low energy regions. Given $H_{max}$ the maximum of the isotropic energy landscape at the barycenter of the simplex and $t_s$ the time step of the last surprise episode, it is possible to define $\hat{H}_{max}(t, t_s)$ the maximum of the energy landscape at time $t \geq t_s$:

$$\hat{H}_{max}(t, t_s) = \begin{cases} H_{max}, & \text{if } t - t_s \geq S_{decay} \\ H_{max}\left[S_a + \frac{(t - t_s)(1 - S_a)}{S_{decay}}\right], & \text{otherwise} \end{cases} \qquad (12)$$

With $S_a \in [0,1]$ as the penalization factor, and $S_{decay} > 0$ the surprise decay, i.e the period of time over which the state of surprise persists, the effect being damped linearly.

$$V(\mathcal{T}) = -\left(1 - \max_i [P(D_i = T | E)]\right)\sum_k \hat{P}(D = d_0 | \varepsilon)\log\hat{P}(D = d_0 | \varepsilon). \qquad (13)$$

FIG. 4 shows a simplex and the cost flow from a series of 9 different questions. The energy relates to the greyscale.

While it will be appreciated that the above embodiments are applicable to any computing system, an example computing system is illustrated in FIG. 7, which provides means capable of putting an embodiment, as described herein, into effect. As illustrated, the computing system 500 comprises a processor 501 coupled to a mass storage unit 503 and accessing a working memory 505. As illustrated, a structured VOI model 513 is represented as software products stored in working memory 505. However, it will be appreciated that elements of the structured VOI model 513, may, for convenience, be stored in the mass storage unit 503. Depending on the use, the survival analysis model 513 may be used with a chatbot, to provide a response to a user question that requires the survival analysis model.

Usual procedures for the loading of software into memory and the storage of data in the mass storage unit 503 apply. The processor 501 also accesses, via bus 509, an input/output interface 511 that is configured to receive data from and output data to an external system (e.g. an external network or a user input or output device). The input/output interface 511 may be a single component or may be divided into a separate input interface and a separate output interface.

Thus, execution of the structured VOI model 513 by the processor 501 will cause embodiments as described herein to be implemented.

The structured VOI model 513 can be embedded in original equipment, or can be provided, as a whole or in part, after manufacture. For instance, the structured VOI model 513 can be introduced, as a whole, as a computer program product, which may be in the form of a download, or to be introduced via a computer program storage medium, such as an optical disk. Alternatively, modifications to existing survival analysis model software can be made by an update, or plug-in, to provide features of the above described embodiment.

The computing system 500 may be an end-user system that receives inputs from a user (e.g. via a keyboard) and retrieves a response to a query using the structured VOI model 513 adapted to produce the user query in a suitable form. Alternatively, the system may be a server that receives input over a network and determines a response. Either way, the use of the structured VOI model 513 may be used to determine appropriate responses to user queries, as discussed with regard to FIG. 1.

Implementations of the subject matter and the operations described in this specification can be realized in digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of methods and systems described herein may be made without departing from the spirit of the inventions. The accompanying claims and their equivalents are intended to cover such forms of modifications as would fall within the scope and spirit of the inventions.

To supplement the above description, the following are provided:

Exact Transformations

In an embodiment, to measure the exact transformation, the state at t is evaluated by simulating the answer.

State Representation

The state $s_t$ of a patient flow at time t must then be represented in the embedding space. Here two classes of methods to embed the current state are presented, based on the type of input vector they exploit.

The first class of methods exploit the disease vector (either the rank, or the marginals), and the second class of method exploit the evidence set.

Using the Past n-Questions

It is also possible to use the average over the past n-questions as the state, where n is an integer of at least 2.

Using the Disease Vector

Once the diseases are embedded in a metric space the disease vector dr can be used to produce a state vector in that new space.

Using Top-N Diseases Set

Given a top-N disease set $D_t=\{d_1; : : : ; d_N\}$ a function $f_d$: $D_t \to s_t$ is defined which maps the top-n disease set to the state vector $s_t$ at time t by averaging the disease embeddings $T_{di}$ of each disease $d_i \in D_t$, such that:

$$f_d(D_i) = \frac{1}{N} \sum_{d_i \in D_i} T_{d_i}$$

and $s_t = f_d(D_t)$

Using Disease Marginal Posteriors Vector

Given a top-N ranked disease vector $D_t=\{d_0; : : : ; d_N\}]$ and its corresponding marginal posteriors vector ranked in the same order $M_t=[0; 1]^N$ a function $f_d$: $(D_t, M_t) \to s_t$ is defined which maps the top-n disease set to the state vector $s_t$ at time t by computing the average of disease embeddings $T_{di}$ of each disease $d_i \in D_t$, weighted by the disease marginals normalised to sum to 1, such that:

$$f_d(D_t) = \frac{1}{\|M_t\|_1} \sum_{i=1}^{N} M_t^i \times T_{D_t^i}$$

and $s_t = f_d(D_t)$

The Question Cost

Once the transformation associated with the evaluated question is known, a cost can be associated to the question using different methods.

The Energy Space

Then the cost of a question can be represented by the max delta energy along the path of the transformation in the energy landscape, or simply the delta energy between the two state.

Below are presented methods of computing the cost on isotropic Hamiltonians but it is worth noting that non-isotropic landscapes (e.g. a slight depression around the barycentre) can also be used.

Computing the Cost on Isotropic Hamiltonians

Relying on the isotropic property of the landscape and defining the cost as the maximum cost along the path reduces greatly the computational cost of exploring the geodesic of the energy landscape. A simple heuristic to compute the cost is defined as follows. Consider that the state $s_t$ lies on a hypersphere S of radius $\|s_t-c\|_2$ with c the center of the simplex. Defining the cost $\Delta H_t^{max}$ as the maximum cost along the path of the transformation and assuming that the energy landscape is isotropic with respect to the center of the simplex, three possible situations might arise depending on the next state $s_{t+1}$:

1. The new state is below or on the tangent to the hypersphere at $s_t$, that $$(s_{t+1}-s_t)\cdot(s_t-C) \geq 0 \tag{14}$$

In that case the cost is simply $\Delta H_t^{max}=H(s_{t+1})-H(s_t)$ which will be negative as the new state is farther from the center.

2. The new state is inside the sphere but did not cross the mid point of the chord l of length d lying on the hyperplane h defined as:

$$h = s_t + \alpha u \tag{15}$$

With $a \in \mathbb{R}$ and U the unit transformation vector defined as:

$$U = \frac{v_\alpha(S_t, T_q, a_q)}{\sqrt{\|v_\alpha(S_t, T_q, a_q)\|_2}} \tag{16}$$

Here list $\|s_t-c\|_2 < d/2$, that is the distance between the two states is smaller than half the length of the chord. In that case the new state $s_{t+1}$ will be at the highest energy point of the path and the cost is defined as $\Delta H_t^{max}=H(s_{t+1})-H(s_t)>0$. $\Delta H_t^{max}$ will be positive as the new state is closer to the center.

3. Finally, if the new state is above the tangent and outside the hypersphere i.e $\|s_t-c\|_2 > r^2$ or it is inside the sphere and crossed the mid-point of l, that is $\|s_t-c\|_2 \geq d/2$ then the maximum energy point will be the midpoint ml of the chord l and the cost will be $\Delta H_t^{max}=H(s_{t+1})-H(s_t)$. The cost will again be positive given that the midpoint is closer to the center.

Computing the Chord Length d

Here, $s_t$ and $s'_t$ are defined as the intersection points between S and h and d the chord length between the two points is computed using the quadratic formula.

Since $s'_t$ is on the sphere:

$$\|S'_t - C\|_2^2 = r^2 \tag{17}$$

Then expressing $s'_t$ as the intersection point on the chord of length d along U:

$$s'_t = s_t + dU \quad (18)$$

$$\|s_t + dU - C\|_2^2 = r^2 \quad (19)$$

And solving for d:

$$d = U^T C - S_t^T U \pm 2\sqrt{(S_t^T U - U^T C)^2 - \|S_t\|_2^2 - \|C\|_2^2 + 2S_t^T C + r^2} \quad (20)$$

Definition of the Hamiltonian H

In an embodiment, a Hamiltonian isotropic from the center of the simplex is proposed:

L1 Landscape

A simple Hamiltonian can be defined as:

$$H(X) = H_{max} \times \left(1 - \frac{\|X - C\|_1}{\|V_i - C\|_1}\right) \quad (21)$$

L2 Landscape $$H(X) = H_{max} \times \left(1 - \frac{\|X - C\|_2}{\|V_i - C\|_2}\right) \quad (22)$$

Quadratic Landscape $$H(X) = H_{max} \times \left(1 - \frac{\|X - C\|_2^2}{\|V_i - C\|_2^2}\right) \quad (23)$$

With $v_i$ the position of any vertex, and c the center of the simplex.

Embedding Questions

Questions asked to the patient may be associated with one or several evidence nodes. It is possible to embed each question over the two simplexes.

The invention claimed is:

1. A computer-implemented method for providing a computer-implemented medical diagnosis via a computer, the computer being configured to generate questions to ask to a user when performing the diagnosis, the computer comprising a memory, and the method comprising:
   constructing an energy landscape as a semantic space for the questions,
   wherein the semantic space is represented by at least one semantic simplex defining an embedded space;
   embedding nodes of a probabilistic graphical model (PGM) in said embedded space,
   wherein the PGM comprises probability distributions and relationships between evidence and diseases, and
   wherein the evidence comprises symptoms and risk factors, the PGM further comprising evidence nodes relating to risk factors and symptoms and disease nodes;
   receiving, at the computer from a user device, an input from the user comprising at least one symptom of the user;
   providing the at least one symptom as the input to a medical model comprising said PGM, the medical model being stored in the memory,
   wherein the at least one symptom is provided to the PGM by activating an evidence node in the PGM corresponding to the at least one symptom,
   performing Bayesian inference utilizing an inference engine on said PGM to calculate an expected information gain of activating each node of a set of further evidence nodes;
   retrieving, from the memory, embedded evidence nodes of the PGM,
   wherein the embedded evidence nodes correspond to evidence nodes of the PGM that have been embedded in said semantic space;
   calculating a cost, for each of the embedded evidence nodes of the set of further evidence nodes, of moving through the energy landscape of the semantic space from an embedded state vector in the semantic space to an embedded evidence node,
   wherein the embedded state vector is determined from a previous question asked by the computer to the user;
   ranking said set of further evidence nodes using, for each node, said calculated expected information gain penalized by the calculated cost of moving through the energy landscape of the semantic space from the embedded state vector;
   using said ranked further evidence nodes to select a next question to be provided by the computer to the user; and
   outputting said next question to the user through the user device.

2. The method according to claim 1, wherein vertices of the at least one semantic simplex represents a location in said embedded space of independent semantic properties, and wherein a dot product of two elements at distinct vertices is null.

3. The method according to claim 1, wherein the embedded space is selected from at least one of Pathogenesis and body systems.

4. The method according to claim 1, wherein said nodes are embedded in said at least one semantic simplex.

5. The method according to claim 1, wherein the cost is calculated by assuming that the at least one semantic simplex defines a fixed energy landscape.

6. The method according to claim 1, wherein the cost is calculated by assuming that the at least one semantic simplex defines a dynamic energy landscape.

7. A system for providing a computer-implemented medical diagnosis, the system being configured to generate questions to ask a user when performing diagnosis, the system comprising a processor and a memory, the processor being adapted to:
   construct an energy landscape as a semantic space for the questions,
   wherein the semantic space is represented by at least one semantic simplex defining an embedded space;
   embed nodes of a probabilistic graphical model (PGM) in said embedded space,
   wherein the PGM comprises probability distributions and relationships between evidence and diseases, and
   wherein the evidence comprises symptoms and risk factors, the PGM further comprising evidence nodes relating to risk factors and symptoms and disease nodes;
   receive, at the computer from a user device, an input from the user comprising at least one symptom of the user;
   provide the at least one symptom as the input to a medical model, the medical model being stored in the memory,
   wherein the at least one symptom is provided to the PGM by activating an evidence node in the PGM corresponding to the at least one symptom;

perform Bayesian inference on said PGM to calculate an expected information gain of activating each node of a set of further evidence nodes;

retrieve, from the memory, embedded evidence nodes of the PGM, wherein the embedded evidence nodes correspond to evidence nodes of the PGM that have been embedded in said semantic space;

calculate a cost, for each of the embedded evidence nodes of the set of further evidence nodes, of moving through the energy landscape of the semantic space from an embedded state vector in semantic space to an embedded evidence node, wherein the embedded state vector is determined from a previous question asked by the computer to the user;

rank said set of further evidence nodes using, for each node, said calculated expected information gain penalized by the calculated cost of moving through the energy landscape of the semantic space from the embedded state vector;

use said ranked further evidence nodes to select a next question to be provided by the computer to the user; and output said next question to the user through the user device.

8. A non-transitory carrier medium carrying computer-readable instructions being adapted to cause the computer to execute the method recited in claim 1.

9. The method according to claim 4, wherein there are a plurality of semantic simplexes, and wherein:

the PGM nodes are embedded in each semantic simplex;

the embedded state vector is provided for each semantic simplex;

calculating the cost of moving in the semantic space from the embedded state vector in the semantic space to each node in the set of embedded evidence nodes is performed for each semantic simplex; and the evidence nodes are ranked, using, for each node, said calculated expected information gain penalized by the calculated cost in each semantic simplex of moving in the semantic space from the embedded state vector.

10. The method according to claim 1, wherein the embedded state is determined from an average embedding of the evidence requested in n previous questions, where n is an integer.

11. The method according to claim 1, wherein performing Bayesian inference using an inference engine on said PGM to calculate the expected information gain of activating each node of a set of further evidence nodes comprises using the inference engine to:

compute posterior marginals of the disease nodes given a current evidence set P(di| E0), and rank the disease nodes to obtain a top set of disease nodes with the highest posterior marginals;

compute the posterior marginals of all unobserved evidence nodes P(ei| E0); and compute the posterior marginals of each evidence node given each disease in the top set P(ei| E0, di)—with assignments ei and di for Ei and Di respectively.

* * * * *